United States Patent [19]

Miller et al.

[11] Patent Number: 5,846,527
[45] Date of Patent: Dec. 8, 1998

[54] CONTINUOUS CELL LINE AND VACCINE AGAINST AVIAN COCCIDIA

[75] Inventors: Timothy J. Miller, Lincoln, Nebr.; Robert A. Clare, Malvern, Pa.; Patricia Lufburrow, Sacramento, Calif.

[73] Assignee: Pfizer Inc, New York, N.Y.

[21] Appl. No.: 848,209

[22] Filed: Apr. 30, 1997

Related U.S. Application Data

[60] Division of Ser. No. 182,004, filed as PCT/US92/05797, Jul. 10, 1992, Pat. No. 5,674,484, which is a continuation-in-part of Ser. No. 729,256, Jul. 12, 1991, abandoned.

[51] Int. Cl.⁶ .......................... A01N 63/00; A01N 65/00
[52] U.S. Cl. .................. 424/93.1; 424/191.1; 424/265.1; 424/271.1; 514/2; 530/350
[58] Field of Search ............... 424/93.1, 191.1, 424/265.1, 271.1; 530/350; 514/2

[56] References Cited

U.S. PATENT DOCUMENTS

| | | | |
|---|---|---|---|
| 4,438,097 | 3/1984 | Shirley | 424/271.1 |
| 4,639,372 | 1/1987 | Murray et al. | 424/267.1 |
| 4,650,676 | 3/1987 | Schenkel et al. | 424/267.1 |
| 4,710,377 | 12/1987 | Schenkel et al. | 424/267.1 |
| 4,724,145 | 2/1988 | Murray et al. | 424/267.1 |
| 4,753,798 | 6/1988 | Kantor et al. | 424/122 |
| 4,874,705 | 10/1989 | Andrews et al. | 435/252.33 |
| 4,935,007 | 6/1990 | Bafundo et al. | 604/49 |
| 5,028,694 | 7/1991 | Mewman et al. | 530/350 |
| 5,187,080 | 2/1993 | Andrews | 435/693 |
| 5,403,581 | 4/1995 | Binger et al. | 424/191.1 |
| 5,635,181 | 6/1997 | Harwood et al. | 424/191.1 |

FOREIGN PATENT DOCUMENTS

| | | |
|---|---|---|
| 6586986 | 4/1987 | Australia . |
| 0382531 | of 0000 | European Pat. Off. . |

OTHER PUBLICATIONS

Speer et al., 1989, *Shedding of the immunodominant P20 surface antigen of Eimeria bovis sporozoites*, Infect. Immun. 57:999–1001.

Chamberland et al., 1991, *Use of mouse macrophage cell lines for in vitro propagation of Toxoplasma gondii RH tachyzoites*, P.S.E.B.M. 197:150–157.

Chai, 1989, *Development of Eimeria tenella in MDBK cell culture with a note on enhancing effect of preincubation with chicken spleen cells*, Kisaengchunghak Chapchi, 27:87–100 (abstract).

Gionti et al., 1989, *A continuous line of chicken embryo cells derived from a chondrocyte culture infected with RSV*, Cell Diff. Dev. 27:215–224.

Danforth, H.D et al, Avian Diseases, vol. 30 (1), pp. 37–42, 1985.

Giambrone, J.J. et al, Poultry Science, 1984, vol. 63, pp. 2162–2166.

Jenkins, M.C. et al, Molecular & Biochemical Parasitology, vol. 25(2) Sep. 1987, pp. 155–164.

Patton, W.H., Science, vol. 150, 1965, pp. 767–769.

Rose, ME, Vet. Rec., 1976, vol. 98(24) pp. 481–484, Jun. 12.

Schmatz, D.M., Advances in Cell Culture, vol. 5, pp. 241–265, 1987.

Wishel, M.H., Molecular and Biochemical Parasitology, vol. 21, 1986, pp. 7–15.

*Primary Examiner*—James C. Housel
*Assistant Examiner*—Ginny Allen Portner
*Attorney, Agent, or Firm*—Peter C. Richardson; Paul H. Ginsburg; Alan L. Koller

[57] ABSTRACT

A non-lymphoid continuous cell line adapted for propagation of avian coccidia is provided. This cell line is useful for the production of vaccine antigens for prophylactic treatment of poultry, particularly in a novel vaccine for coccidia.

10 Claims, No Drawings

CONTINUOUS CELL LINE AND VACCINE AGAINST AVIAN COCCIDIA

This is a division, of application Ser. No. 08/182,004, filed Jul. 11, 1994, now U.S. Pat. No. 5,674,484 which is the U.S. national stage of PCT/US92/05797, filed Jul. 10, 1992, which is a continuation-in-part of application Ser. No. 07/729,256, filed Jul. 12, 1991, now abandoned.

FIELD OF THE INVENTION

The present invention relates generally to a virus-free continuous cell line adapted for propagation of avian coccidia. More particularly, the invention relates to the use of the cell line for the production of vaccine antigens for prophylactic treatment of poultry against coccidiosis.

BACKGROUND OF THE INVENTION

Coccidiosis is an enteric disease of domestic and wild livestock causing acute morbidity resulting in decreased growth and feed utilization. The avian coccidia (Genus Eimeria) are obligate intracellular protozoan parasites of the intestinal epithelium. These parasites have a monoxenous life cycle and exhibit a high degree of host-species and tissue specificity. For poultry, coccidial infection results in economic loss from stunting and skin discoloration. Overall, the combination of losses due to coccidiosis and prophylactic medication results in a cost to the poultry industry in excess of $300 million annually [Danforth and Augustine, Animal Nutrition and Health, pp. 18–21 (August 1985)].

Thousands of coccidian oocysts may be ingested at one time by a single host. Once ingested the parasites invade specific intestinal cells where they may undergo several rounds of asexual replication followed by gametogeny before millions of new parasites are shed in the litter to complete the life cycle. Different species of poultry suffer from infections caused by different coccidia species. The domestic fowl (Gallus domesticus) can be infected by any of the coccidia *Eimeria tenella, E. necatrix, E. brunetti, E. maxima, E. acervulina* and *E. praecox*. The following coccidia are implicated in infections of turkeys (Meleagris): *Eimeria meloagrimitis, E. dispersa, E. meleagridis, E. gallopavonis, E. adenoides, E. innocua* and *E. subrotunda*. Domestic ducks (Anas) suffer from infections caused by *Tyzzeria perniciosa* and also, it is believed, by *Eimeria anatis* which they can acquire from wild ducks (Anas platyrhyncos). Geese (Anser) can suffer from infections caused by *Eimeria anseris, E. nocens* and *E. parvula,* and in addition it is believed that domestic geese can acquire infections from Canada geese caused by *Eimeria hermani, E. striata* and *E. fulva*.

Immunity to coccidiosis is reported to be highly species-specific and a manifestation of cell-mediated processes [M. E. Rose, in "Biology of the Coccidia", P. L. Long, ed., University Park Press, Baltimore, pp.328–372 (1982)]. Natural exposure to Eimerian oocysts elicits complete protective immunity; this response appears to result primarily from the development of intracellular parasite stages instead of extracellular sporozoites or merozoites [M. Jenkins et al, *Infec. Immun.*, 59:4042–4048 (1991)]. Although a few oocysts may confer protection to subsequent challenge, this primary exposure impacts adversely on weight gain, feed utilization and skin pigment retention.

Current methods of control involve primarily chemotherapeutic treatment with anticoccidial drugs mixed into the feed. Effective compounds have included sulphonamides, quinolines and polyether ionophorous antibiotics [See, e.g., L. R. McDougald, in "Biology of the Coccidia", pp. 373–427 (1982)]. These compounds appear to affect parasite development at different stages of their lifecycle. Over time, however, drug resistant strains of parasites have evolved, thus severely limiting a drug's usefulness [T. K. Jeffers, *Avian Dis.*, 18:74 (1974); T. K. Jeffers, *Avian Dis.*, 18:331 (1974); and H. D. Chapman, *Vet. Parasit.*, 15:11–27 (1984)].

Other less established control measures include the actual feeding of live oocysts from well characterized wild type or attenuated strains of several Eimeria species to chickens to establish immunity. Cocci-Vac [Sterwin Labs] utilizes controlled numbers of specific species of chicken Eimeria added to feed or water or administered individually [See, e.g., S. A. Edgar, Research in Coccidiosis, McDougald et al, eds., University of Georgia, p. 617 (1986)].

Another approach to the development of a live vaccine includes the administering of attenuated parasite strains. Selection for early oocyst development or precociousness results in strains having abbreviated asexual development, and reduced pathogenicity [See, Shirley et al, *Avian Path.*, 15:629 (1986); Shirley et al, *Res. Vet. Sci.*, 44:25 (1988); and European Patent No. 0256878-A2]. Serial passaging of Eimeria species in chicken embryos also results in strains of reduced pathogenicity [Long, *J. Comp. Path.*, 82:429 (1972); and Long, *J. Comp. Path.*, 82:439 (1972)].

Both attenuation practices have been used in combination with a "trickle dose" method of administration to achieve effective immunity [Johnson et al, "Research in Coccidiosis", McDougald et al, eds., University of Georgia, pp. 634–641 (1986)]. Although this method has been shown to be useful for vaccination, it requires introduction and maintenance of live parasites in a poultry operation that presents an inherent risk of reversion to pathogenicity.

While active infection generates a protective immune response, effective immunization with killed parasitic stages or structural antigens is less clear. Early studies indicated that antigen extracts from dead parasites were not immunogenic [Long et al, *Exp. Parasitol.*, 16:1 (1965); Rose et al, "Vaccines Against Parasites", Taylor and Muller, eds., Blackwell Scientific Publications, Oxford, pp. 57–74 (1980)).

In contrast, European Patent Application No. 0167443 describes an extract produced from sporulated *E. tenella* oocysts, which when injected intramuscularly, protected chickens against homologous parasite challenge. A similar extract produced from *E. acervulina* oocysts is described in U.S. Pat. No. 4,724,145 which elicits a protective response to challenge with that parasite, as well as *E. maxima* and *E. tenella*. An excysted extract of *E. tenella* sporozoites in an aqueous suspension for subcutaneous administration is described in U.S. Pat. No. 4,808,404.

European Patent Application No. 0135712 describes solubilized *E. tenella* sporozoite antigens as effective immunogens; while European Patent Application No. 0135073 refers to the use of antigens from solubilized *E. tenella* merozoites as immunogens. European Patent Application No. 0291173 describes sporulated *E. tenella* extracts for injection into the egg of the bird prior to hatching to induce immunity. U.S. Pat. No. 4,863,731 describes the use of an aqueous concentrate of viable sporulated oocysts from at least one species of coccidia as a feed additive.

In addition, antigen extracts from gametocytes of *E. maxima* are being examined for potential immunogenicity (See, e.g., European Patents No. 0256514 and 0256536]. Although varied degrees of immunity have been demonstrated with the above preparations, their preparation is highly labor intensive and manufacturing practices are difficult on a large scale.

Recent and more practical approaches to vaccine development involve the production and characterization of genetically engineered antigens [Binger et al, *J. Cell Biochem.*, 10A:144 (1986); Brothers et al, *Mol. Biochem. Parasitol.*, 28:235 (1988); Danforth et al, *Avian Dis.*, 30:37 (1985); Jenkins et al, *Exp. Parasitol.*, 66:96 (1988); European Patent Application No. 0164176; European Patent Application No. 0337589 and Australian Patent Application No. 65867/86]. These procedures require the isolation of mRNA from sporozoites or merozoites, the production of a cDNA library, screening of the cDNA library with an appropriate antibody, and the subsequent cloning into an expression vector. The resultant cloned antigens can then be produced in large quantities in microbial fermenters.

Few immunogenicity studies have been reported to date, but suggest partial protection is elicited by these antigens [Danforth and Augustine, supra; Jenkins et al, supra]. Overall, these cloned structural proteins induce incomplete protection at best and their immunizing capability depends in part on host genetics [Clare, *Infect. Immunol.*, 57:701 (1989)].

Finally, passive immunizations with monoclonal antibodies produced against *E. tenella* sporozoites [U.S. Pat. No. 4,710,377] and active immunizations with anti-idiotypic monoclonal antibodies [European Patent No. 0241139] derived from *E. tenella* sporozoites are being investigated.

The advancement of knowledge on host/(protozoan) parasite interactions has been hampered by the lack of adequate in vitro cell culture systems in which to maintain parasites. Both mammalian and avian coccidia are very difficult to grow in vitro, with the exception of *Toxoplasma gondii*, which grows well in a variety of primary cultures and established cell lines [D. J. Doran, in "The Biology of the Coccidia", pp. 253–257 (1982)].

In vitro propagation of Eimeria has to date been limited. The entire prepatent coccidia development from sporozoite to oocyst, has only been obtained with *E. tenella*, and only in primary avian kidney cells [Doran et al, *J. Protozool.*, 20:658 (1973)]. However, the primary chicken kidney epithelial cell system is not compatible with manufacturing protocols and has limitations for use as a research assay system.

Only one established cell line, Madin Darby Bovine Kidney (MDBK) has been reported to support Eimerian growth in vitro, but the coccidia develops only through one generation of asexual development [D. M. Schmatz, *Adv. Cell Culture*, 5:241 (1987)].

Oocysts have been obtained from avian *E. acervulina* [M. Nacri-Bontemps, *Ann. Rech. Vet.*, 7:223 (1976)] and *E. meleagrimitis* [Augustin et al, *J. Protozool.*, 25:82 (1978)] as well as the bovine *E. bovis* [Speer et al, *Z. Parasitenkd*, (1973)] when initial host-derived merozoites have been used as the inoculum.

To date, no established cell line has been reported to support Eimerian growth beyond the first generation of asexual development. There remains a need in the field of prophylactic and therapeutic treatment of various avian pathogenic infections for an established cell line capable of propagating in vitro components of Eimeria species, to provide safe and effective vaccines against these pathogens, including coccidia.

SUMMARY OF THE INVENTION

As one aspect, the present invention provides a novel continuous cell line, SB-CEV-1\P, which is capable of propagating avian coccidia. Also described are clones derived from this cell line.

Also part of this aspect of the invention are three additional cell lines propagated from the aforementioned parental cell line. These cell lines are referred to as SB-CEV-1\F7, SB-CEV-1\G7, and SB-CEV-1\A2. Clones, or sub-clones, derived from these cell lines are also encompassed by this invention.

As another aspect, the present invention provides the above cell lines persistently infected with an avian parasite, particularly a Coccidial parasite.

A further aspect of the present invention involves a novel method of vaccine development in which coccidia antigens are produced at various stages of asexual or sexual development by culturing one of the infected cell lines and harvesting cell culture components for use in vaccine compositions.

Yet another aspect of the present invention is a multicomponent vaccine comprising selected pathogenic antigen compositions from various avian coccidia pathogens produced through use of the cell lines described herein.

Still a further aspect of the present invention is a vaccine for coccidiosis capable of inducing host protection against infection in poultry containing one or more of the vaccine compositions described above in association with suitable carriers and adjuvants.

Still a further aspect of this invention is a novel method for vaccinating poultry against infection by parasites causing coccidiosis involving administering to an animal an effective dose of the above-described vaccine compositions.

Also involved in this invention is a method for producing a recombinant antigen by transfecting the cell line with a recombinant DNA molecule encoding an exogenous protein under control of a suitable expression control sequence; and culturing the stably transfected cell line under suitable culture conditions to produce the recombinant antigen.

Another aspect of this invention provides a method of drug screening for agents which destroy or inhibit the growth of the selected intracellular parasites comprising exposing the infected cell line of this invention to a selected anti-infective agent, and examining any effects on the pathogen.

Other aspects and advantages of the present invention are described further in the following detailed description of preferred embodiments of the present invention.

DETAILED DESCRIPTION OF THE INVENTION

The present invention provides methods and compositions for prophylactic vaccination of Aves against infection by avian pathogens and parasites, particularly for the treatment and control of coccidia in poultry. "Poultry" is defined herein to include birds of the order Galliformes, such as the ordinary domestic fowl or chicken (Gallus domesticus), turkeys (Meleagris), pheasants (Phasianus), partridges (Pedrix), grouse (Lagopus), guinea fowl (Numida) and peacocks (Pavo), and also birds of the order Anseriformes, such as ducks (Anas) and geese (Anser).

This invention provides a novel continuous cell line SB-CEV-1\P, described in detail in Example 1 below. This cell line has 42 chromosomes per cell, and is reverse transcriptase negative. The cell line is characterized as containing only a low incidence of non-infectious viral particles (type A) associated with the endoplasmic reticulum. The cell line is also negative for endogenous mammalian pathogens, and has no indication of avian leukosis virus. Further the cell line has no contamination with mycoplasma, bacteria or fungi. Thus the cell line is free of mammalian and avian viruses.

This cell line also has functional characteristics which associate it with avian background. For example, this cell line replicates at 41° C., characteristic of avian cells and it has unique nutritional requirements for maintenance in vitro. Further, the novel cell line of this invention is the only existing continuous cell line capable of replicating the prepatent life cycle (i.e., that period between infection and the detection of the parasite in the body) of the avian coccidia, Eimeria, at high levels.

The SB-CEV-1 cell line of this invention has been selected for the production of vaccine antigens, particularly avian coccidia. The cell line also provides substrates for use in the growth of genetically engineered vectors expressing recombinant DNA derived from foreign genes.

Several cell populations have been cloned from this parent cell line. These clones have distinct characteristics for propagation and maintenance of the avian parasite. Further these cloned cell populations, SB-CEV-1\F7, SB-CEV-1\G7, and SB-CEV-1\A2 have a high incidence of multi-nucleated giant cells. The appearance of distinct clones from the parent cell line is also indicative of a multicellular origin, e.g., possible aberrant growth in the chicken viscera used as the origin of the parent cell line. These cloned "progeny" cell lines, however, are also continuous cell lines capable of replicating the prepatent life cycle of the avian coccidia, Eimeria, at high levels. These cell lines are believed to share the same characteristics as the parental strain, and have also shown the ability to propagate Coccidia. This invention, therefore, also encompasses other cell lines which are sub-cloned from, or otherwise derived from, SB-CEV-1\P or from the specifically identified clones of that parent cell line. Such additional progeny clones are anticipated to share significant characteristics of the parent cell line. Thus the sub-clones may be substituted for the parent cell line wherever SB-CEV-1 or SB-CEV-1\P is specifically mentioned throughout this specification. Also, wherever in the following description, a cell line is referred to in the singular, the term "the cell line" or "the SB-CEV-1 cell line", is meant to include SB-CEV-1\P, its subclones SB-CEV-1\F7, SB-CEV-1\G7, or SB-CEV-1\A2, or any other subclones of any of these specifically identified cell lines.

The parent cell line and the subclones thereof of the present invention may be employed to support the in vitro development of avian Eimeria species. While the disclosure below refers specifically to methods and vaccine compositions for E. tenella infections, it should be understood that other avian parasite pathogens, including viruses, as well as other animal species protozoans, may be produced using a cell line of this invention in analogous procedures. Thus the cell line is capable of providing an expression system for a variety of pathogenic antigens and other proteins for use in research, characterization and the production of vaccine components. In addition, as the only existing continuous cell line that replicates the prepatent life cycle of avian Eimeria, the cell offers a unique substrate to study enzymatic and genetic characteristics of a parasite permissive cell line.

The cell line of this invention also provides a means for production of recombinant avian vaccine components, such as subunit antigens derived from reovirus, coronavirus, herpesvirus, para- and orthomycoviruses. The cell line may be transfected by a recombinant DNA molecule or expression vector encoding a selected pathogen protein or peptide under the control of conventional regulatory control sequences, and cultured. The recombinant protein may then be expressed by the cultured SB-CEV-1 cell line or its progeny.

The novel cell line also provides a substrate for replication of other Eimeria species. This continuous cell line of the invention may also be utilized to isolate and characterize independent stage specific components of intracellular parasitic stages. Specifically, this cell line provides the only source of readily available parasite DNA, RNA, and protein from intracellular structures. Further, this cell line may be used to grow other desired, selected pathogens.

The SB-CEV-1 cells of the present invention permit development of the chicken species E. tenella and E. necatrix, as well as development of the turkey coccidia, E. adenoides and E. meleagrimilis. It is expected that the cell line will also permit the development of other species, e.g., E. acervulina and E. maxima.

The presently preferred culture conditions for growth of the cell line include culturing the cell line in Medium 199 [Irvine Scientific] and 5% fetal bovine serum (FBS) (or equivalent such as Optimem and 1% FBS) under incubation conditions of 5% $CO_2$ and 40.5° C. The cells grow more slowly at 37° C. rarely reaching confluency and require at least 10% serum. Other culturing conditions, including media formulations with regard to specific nutrients, oxygen tension and reduced serum, may be employed for growth of these cells, and may be selected and optimized by one of skill in the art.

The novel cell line of this invention, SB-CEV-1\P, was deposited with the American Type Culture Collection, 12301 Parklawn Drive, Rockville, Md. on Jul. 3, 1990 under ATCC No. CRL10497. The development of this cell line is described in detail in Example 1 below. The progeny cell line SB-CEV-1\F7 was similarly deposited on Jul. 3, 1990 under ATCC No. CRL10495. The progeny cell line SB-CEV-1\G7 was deposited on Jul. 3, 1990 under ATCC No. CRL10496. These deposits comply with the requirements of the United States Patent and Trademark Office for microorganism deposits made for patent purposes, and will be made to comply with the requirements of the Budapest Treaty at the time of foreign filing.

The present invention further provides a variety of vaccine components and compositions prepared by the use of the cell line of this invention. A particularly desirable embodiment of this invention is a vaccine composition derived from Eimeria parasites. This vaccine composition may contain whole cell extract (live or inactivated) from the above-described cell lines infected with a selected pathogen, or subfractions thereof. These vaccine compositions may also contain modified cellular or parasitic antigens, produced by modifying the culture conditions of the infected cell line.

In one embodiment, vaccine compositions for use in vaccines to avian coccidiosis are developed by infecting a cell line of this invention with a selected parasite, preferably an Eimeria parasite, e.g., E. tenella. Infection of the cells is monitored by use of an in vitro enzyme-linked immunosorbent assay (ELISA) employing conventionally developed monoclonal or polyclonal antibodies to various life cycle stages of the parasite. The infection may also be measured by a radiolabelled uracil uptake assay. Both the ELISA and uptake assays are described in detail in Example 2 below.

Approximately 72 hours post-infection the cells and medium or extracellular secretions are harvested by collecting cells and/or culture fluids. As an optional step, if necessary, the culture fluids may be inactivated using conventional techniques, such as by sequential freeze/thaw cycles or by the addition of filtration, denaturing or crosslinking agents such as β-propiolactone, formaldehyde or glutaraldehyde.

Various portions of this infected cell culture preparation may be employed in vaccine compositions:

1) the whole preparation without subfractionation;
2) a modified preparation affected by changes in the culture media and conditions (e.g. the omission of serum during critical growth periods, pH or ion changes);
3) subfractionation to produce cell associated soluble components; and 4) subfractionation and modified vaccine components.

One embodiment of a vaccine composition or component according to this invention is prepared by disrupting the infected cells of the above-described culture by scraping. The resulting disrupted cell composition is used for a vaccine preparation without further desiccation or hydration.

As another vaccine component of this invention the above-described vaccine component may be modified by altering the serum concentration or components and other nutritional additives, in the medium employed to culture the parasite-infected cell line of this invention. For example, early stages of the parasite may be arrested by culturing the infected cell line in minimal essential medium, MEM. Alternatively, by substituting chemically defined media, the cell line will permit later stages of parasite development to be employed in the vaccine. Additional nutritional changes to the medium which may affect parasite development and modify the antigenic proteins produced in the cell line of this invention involve the addition or subtraction from the media of one or more of biotin, choline chloride, insulin, or non-essential amino acids.

A modified vaccine component may also be produced in the infected cell line by the application of classical mutagenic techniques, e.g., the addition of alkalating agents, chelating agents, dimerizing agents or outside treatment of the cell line by ultraviolet light during the culture of the infected cell line. These agents may genetically modify the cell and provide it with an altered capacity to produce an abnormal parasite. Alternatively, depending on the stage of development of the parasite within the cell when it is first contacted with the mutagenic agent, the parasite itself may be directly mutagenized for the production of a preferred vaccine component.

Still another embodiment of a vaccine composition for use in prophylactic treatment of Aves, particularly poultry, against Coccidia is prepared by the methods above using subfractions formed by the disrupted cells and the medium from the cell culture. These fractions are obtained by first separating the media from cell fractions, e.g., by centrifugation, size, molecular weight, charge, or various conventional biochemical means. These fractions are then employed as vaccine compositions which may be presented to birds. For example, one fraction of the above-described cell culture is obtained by centrifuging the medium containing the disrupted cells. The medium is removed, and the remaining material pelleted to obtain the cellular components. This pellet is resuspended in fresh tissue culture media. In addition, the supernatant fraction may also be utilized as a vaccine component.

One or more of the above described vaccine components can be admixed or adsorbed with a conventional adjuvant or administered without an adjuvant. The adjuvant is used as a non-specific irritant to attract leukocytes or enhance an immune response.. Such adjuvants include, among others, oil and water, aluminum hydroxide, muramyl dipeptide, killed Bordetella and saponins, such as Quil A. Presently, the preferred adjuvant is Amphigen (Hydronics Inc.; U.S. Pat. No. 5,084,2693.

A preferred vaccine dosage is between approximately 0.05 μg–100 μg of parasite protein. Other appropriate therapeutically effective doses can be determined readily by those of skill in the art based on the above immunogenic amounts, the condition being treated and the physiological characteristics of the animal. Accordingly, a pharmaceutical preparation provides a unit dosage of between 0.1 to 2 mls of a sterile preparation of an immunogenic amount of the active vaccine components, or a combination thereof. In the presence of additional active agents, these unit dosages can be readily adjusted by those of skill in the art.

A desirable dosage involves administration of 1 to 2 doses of desired vaccine composition, where the antigenic content of each fraction is desirably as stated above. The mode of administration of the vaccines of the invention may be any suitable route which delivers the vaccine to the host. However, the vaccine is preferably administered subcutaneously. However, the vaccine may also be added to feed or water for ingestion in the form of a suspension. Other modes of administration may also be employed, where desired, such as intradermally, intravenously, or intramuscularly.

It will be understood, however, that the specific dose level, mode and timing of administration for any particular animal will depend upon a variety of factors including the age, general health, and diet of the animal; the species of the animal; synergistic effects with any other drugs being administered; and the degree of protection being sought. Of course, the administration can be repeated at suitable intervals if necessary or desirable.

In preliminary tests of these vaccines, bird performance is enhanced. Preliminary results show that the above-described vaccine, which was formed by simply decanting conditioned media or disrupting the SB-CEV-1 cells, and harvesting by centrifugation the cell fluids, enhances bird performance during challenge. Additionally the subfraction vaccine described above also has shown efficacy in an in vivo assay. The in vivo tests are conducted as follows. Chicks two weeks of age are immunized subcutaneously with 1 ml of culture media harvest. Two weeks later, the chicks are challenged with 10,000 oocysts of *E. tenella*. For the next 6 days, the chickens are monitored for aspects such as weight gain and feed efficiency. Intestinal lesions are thereafter screened and subjects are scored on this basis. This assay is described in more detail in Example 4 below.

In addition to the use of the cell lines of this invention for the development of vaccines, these cell lines may also be used in methods for screening anti-parasitic agents in the development of new anti-coccidia drugs. For example, cultures of infected cells may be conventionally labeled, e.g., with a radioactive molecule. The selected drug for testing may then be incorporated into the cell cultures. The cell culture may then be harvested at discrete intervals post infection, and label incorporation of the radioactive precursor may be determined by harvesting and processing for scintillation counting. An example of such drug screening employing alpha-amanitin as the test drug is described in detail in Example 5 below. If a drug is effective at a particular dose or time of administration, the incorporation of counts (parasite material) should be halted. If no inhibition of label incorporation is observed, the drug is ineffective in controlling the parasite infection in vitro.

Other conventional drug screening modes known to those of skill in the art may also be employed using the cell lines of this invention.

The following examples illustratively describe the production of the novel continuous cell lines of this invention. These examples are for illustration only and do not limit the scope of the present invention.

EXAMPLE 1

Isolation of Parental Cell Line, SB-CEV-1\P, and Clones SB-CEV-1\F7 and SB-CEV-1\G7

SB-CEV-1 cells were isolated from an abnormal tissue mass (approximately 1 cm×2 cm) associated with the visceral connective tissue of one 20 day old SPAFAS [COFAL-24] chicken embryo. The tissue was aseptically removed and rinsed in Hank's Basic Salt Solution (HBSS) containing 1% Fungi-Bact Solution [Irvine Scientific, Irvine, Calif.]. The tissue was minced with scissors, then enzymatically dissociated using 0.25% trypsin (1:250) in HBSS. The dissociated cell suspension was collected in a 50 ml centrifuge tube containing 0.5 ml fetal bovine serum to inactive the trypsin and centrifuged at 700 g for 10 minutes.

The cells were resuspended in 5 ml Weymouth's MAB87/3 media [Irvine Scientific] supplemented with 8 mg/l bovine insulin [Collaborative Research, Inc., Bedford, Mass.], 12 ml/l 200 mM L-glutamine and 1% Fungi-Bact Solution [Irvine]. This 5 ml volume was pipetted into a 25 cm$^2$ Corning tissue culture flask and incubated at 40.5° C. in 5% $CO_2$. After 24 hours of incubation, the media was changed. This primary culture contained numerous explants with centers of epithelial-like cells and radiating fibroblasts.

After 72 hours, the near-confluent culture was washed once with $Ca^{++}/Mg^{++}$-free phosphate buffered saline (PBS) then treated with 0.02% ethylene diamine tetraacetic acid (EDTA) in HBSS to dissociate the cells. The resulting cell suspension was decanted, the cells were collected by centrifugation and resuspended in the MAB87/3 media formulation used previously. This culture was then split 1:10, creating passage-1 (P1) by plating cells in seven 25 cm$^2$ culture flasks and two 60 mm$^2$ petri dishes. Cultures were incubated as before.

Media was changed on actively growing cultures at 72 hours omitting fetal bovine serum (FBS). The media in one flask was replaced with Medium 199 [Irvine Scientific] supplemented with 10% FBS. After an additional 48 hour incubation, the culture containing Medium 199 showed actively growing cells, while the MAB87/3 cultures were static. Returning serum to these cultures up to 10% did not promote cell growth to the level observed using Medium 199. Therefore, all subculturing was done, hereafter, in Medium 199 plus 10% FBS.

Further subculturing was done (Passage-2 to Passage-11) when flasks reached confluency. With increasing passage number, cells grew more slowly, became fibroblastoid and highly vacuolated and released debris into the media. Additional media formulations (EMEM+10% FBS; RPMI 1640+ 10% FBS; DMEM/Ham's F-12+5% FBS) were tested on these cells to forestall or counteract this pending senescence. However, cells showed the least deterioration in Medium 199. Cells from several passages (P4, P5, P6, P7, P9, P10) were frozen down in liquid nitrogen. These cells appeared to reach crisis at P11–13 and died.

One 75 cm$^2$ flask of P11 cells containing a very few isolated foci of cells was repeatedly fed with Medium 199 and 10% FBS for 58 days after its last subculturing. At this point, fibroblast-like cells began to grow outward from these foci. After an additional 15 days, cells in this T-75 flask reached confluency and were split 1:2 creating P12.

Subculturing has continued to the present in Medium 199 [Gibco Laboratories, Grand Island, N.Y.], 3.43 ml/l of 200 mM L-glutamine and 1% Antibiotic-Antimycotic [Gibco Laboratories] using the passage criterion of splitting 1:20 every 7 days. The cells have lost all epithelial characteristics and are distinctly fibroblast-like in morphology. Other media formulations used successfully since crisis include Weymouth's MAB87/3 and 5% FBS, Dulbecco's MEM [Gibco Laboratories] and 5% FBS and MEM with Earle's salts [Gibco Laboratories] and 5% FBS. The FBS requirement has been reduced to 5% for SB-CEV-1 cells of passage 24 which were subjected to subcloning by dilution using single-cell isolation in 96 well microculture plates. This technique produced 25 clones from the parental cell line SB-CEV-1\P in unconditioned Medium 199 with 5% FBS. Of these clones, two, designated SB-CEV-1\F7 and SB-CEV-1\G7, showed an exceptional capacity to support asexual development of E. tenella.

These two clones along with the parental line, SB-CEV-1\P have been deposited with the ATCC as identified above. Passage No. 10 was deposited for both clones and passage No. 20 for the parental line. Freezing has not had any deleterious effect on cell performance as several frozen samples have been restored successfully. Standard biologic quality control was satisfactory from P33 of the parent line. In addition, the parent line shows a karyotype of approximately 42 chromosomes, is reverse transcriptase negative, does not express avian retroviruses (e.g. avian leukosis), does not express other endogenous pathogens (mammalian or avian), is tumorigenic in nu/nu mice, and shows no bacterial, fungal or mycoplasma contamination. A low incidence of A-type viral particles associated with the endoplasmic reticulum was resolved by transmission electron microscopy. The parent line as well as both clones showed isoenzyme focusing profiles similar to BHK-21 cells [National Veterinary Services Laboratory] and dissimilar to SL29 cells (a transformed chicken fibroblast line) [ATCC No. CRL1590] for the enzymes lactose dehydrogenase, malate dehydrogenase, nucleoside phosphorylase, peptidase A and phosphoglucomutase. In contrast, both clones and the parent SB-CEV-1 line are morphologically distinct from BHK-21 and ACC-111 cells. In addition, the SB-CEV-1 cell lines show a high incidence of multinucleated giant cells. Most importantly, the SB-CEV-1 cells produce high levels of parasite material from different stages of the Eimeria prepatent life cycle.

EXAMPLE 2

Assays to Monitor Parasite Development in the Cell Line

A. The direct sporozoite-based enzyme linked immunosorbent assay for detection of coccidia proteins (SPZELISA) involves the adherence of antigen (e.g., supernatants from uninfected or infected F7 cells or disrupted sporozoites (SPZ) or merozoites) in twofold serial dilutions to the well of a 96-well tray. Antibodies which recognize SPZ antigens bind to the antigen in a dose related response. After the primary antibody is bound, a second antibody produced in goats against rabbit IgG which is also biotinylated is added. Again, this anti-rabbit antibody will bind to the rabbit #15, 16 anti-SPZ antibody previously bound to antigen in the wells. The anti-SP2 antibodies were produced as follows. Purified sporozoites (described below) for E. tenella were suspended in serum free media at a concentration of 2–5×10$^6$ sporozoite per ml. An equal volume of Freunds Complete Adjuvant was added mixed and 0.5 ml was inoculated subcutaneously at 2–4 sites on the back of 6 kg New Zealand white rabbits (mixed sexes). Booster inoculations were given in a similar manner using Incomplete Freunds Adjuvant at 2 to 4 week intervals (3 inoculations minimum). Blood was collected in serum vacutainers (Becton-Dickenson) two weeks after third inoculation. The serum was allowed to clot at room temperature for 1 hour and then was centrifuged at 2000 rpm for 10 minutes to pellet the clot. The serum was removed, aliquoted into 1.5 ml per tube and stored at −20° C. After the secondary antibody is bound, an enzyme-labelled streptavidin which binds to biotin is added. Substrate is incubated and the enzyme linked to streptavidin bound to the well will convert the substrate to a visible form. The amount of color measured is proportional to the amount of antigen cross-reactive to SPZ proteins in the test supernatant. Included on the plate are samples containing antigens from uninfected supernatants as a negative control as well as sonically disrupted SPZ. This sporozoite material serves as a positive control and is used to generate a standard curve against which parasite antigens in infected supernatants are measured. In this manner, parasite-specific material in infected cell supernates can be quantitatively assessed and compared.

Approximately fifty 3–4 week old birds are each infected orally with 100,000 E. tenella oocysts. Cecal pouches are harvested at approximately 7.5 days and lumen contents subjected to pepsin digestion. Oocysts then undergo sporulation in 2.5% potassium dichromate for 3–4 days and are sterilized by chlorine bleach. The sterilized oocysts are stored at 4° C. in Medium 199+2x antibiotic. Generally, fifty birds yield approximately $5 \times 10^9$ oocysts. This protocol is repeated every 3–4 weeks to maintain virulence.

Cell culture antigen for the assay is produced according to the following modified excystation procedure. The sporocysts are purified by breaking 10 ml oocysts (at $3 \times 10^7$/ml) with 5 ml 0.5 $\mu$m glass beads in a small chamber bead beater and separating the debris using 0.75M sucrose in PBS followed by centrifugation using 50% isotonic Percoll. Using a solution consisting of 4% (w/v) tauradeoxycholic acid, 0.25% (w/v) trypsin, HBSS, and adjusting to pH 8.0 with bicarbonate, SPZ excystation is performed by incubating this mixture with the purified sporocysts at 40.5° C., 60–90 minutes with vortexing at approximately 15 minute intervals. The SPZ are then collected using 60% isotonic Percoll, the pellet is resuspended in serum-free media and counted. Generally, $3 \times 10^8$ oocysts yields approximately $7.2 \times 10^8$ SPZ (30%). The SPZ are sonicated and stored at −20° C. as a standard source of antigen for the assay.

The antigen seeding is performed as follows. 200 $\mu$l of antigen prepared in 10 mM borate buffer, pH 9.0, is added to the top wells of a 96 well Nunc Immuno plate. All remaining wells contain 100 $\mu$l of the borate buffer alone. Serial 2-fold dilutions are made in rows B–G. Row H contains only buffer and is used as a negative control. The wells are covered with parafilm and incubated overnight at 4° C. The SPZ control is loaded at 10 ng in the top row of wells. Antigen without 1% FBS is loaded at 100 ng and antigen+1% FBS [Gibco] is loaded at 1000 ng. Supernatant antigens from uninfected F7 cells are included as a negative control in each assay. Supernatants harvested at 72 hours from a designated infected passage of F7 cells are also included on each plate as an internal standard. The 72 hours supernatant is first quantitated by the SPZELISA and then its relative value as compared to the SPZ control is used to monitor and adjust for assay-to-assay variability.

Next, supernatants are washed 3× with PBS+0.05% Tween-20 (PBS-T) and blocked by adding 200 $\mu$l of 5% skim milk (Difco) in PBS-T to each well. Wells are incubated 1 hour at 37° C. covered with plastic wrap, and are washed again 3× with PBS-T. The primary antibody is then added. 100 $\mu$l of rabbit anti-SPZ antibodies #15, 16 diluted to 1:20,000 in 0.5% BSA in PBS-T is added per well and the plates are incubated 1 hour at 37° C. covered with plastic wrap. The plates are washed again 3× with PBS-T. Following this, the conjugated antibody, 100 $\mu$l of 1:2000 dilution of biotin-labeled goat anti-rabbit IgG (KP) in 2% skim milk in PBS-T, is added per well. The plates are again incubated 1 hour at 37° C. and then washed 3× with PBS-T. Following this, 100 $\mu$l of 1:1500 dilution of peroxidase-labeled streptavidin [Kirkegaard Perry] in 2% skim milk in PBS-T is added per well. The plates are then incubated 1 hour at 37° C. in the dark and washed 3× with PBS-T. TMB-Peroxidase [Kirkegaard Perry] is mixed in a 1:1 ratio with $H_2O_2$ and 100 $\mu$l of substrate per well is added. The plates are then incubated 15 to 30 minutes at 37° C. in the dark. At the end of the incubation time, 100 $\mu$l of 1M HCl per well is added to stop the reaction. Readings are taken at 450 nm on the Vmax.

B. Another assay employed to monitor parasite development in the cells takes advantage of the parasite's, but not the host's, ability to incorporate radiolabelled uracil into its RNA [D. M. Schmatz et al, J. Protozool., 33:109–114 (1986)]. Briefly, cultures of cells in microtiter plates are seeded at $1 \times 10^5$ cells/ml, 0.1 ml/well, 24 hours prior to infection with E. tenella at $1 \times 10^5$ sporozoites per well. The sporozoites are incubated with the cells for 4 hours at 40.5° C. and then removed by washing with serum-free medium. The cells are then overlaid with medium and serum and incubated for 24 hours. At 24 hours post-infection, the cells are washed and then refed with medium containing [3H]-uracil. Label is incorporated over a 24 hour period and then the cells are collected onto filters using a cell harvester (Cambridge Technology, Inc.). Radioactivity on the filters is determined in a Beckman LS 3801 liquid scintillation counter after the addition of aqueous scintillation cocktail (Beckman Ready Safe). Background counts and radiolabel incorporated into uninfected cells are also measured.

EXAMPLE 3

Avian Vaccines

A. One vaccine formulation is prepared from a SB-CEV-1/P host cell clone seeded at a rate of $1.0 \times 10^5$ cells/ml in a T-150 flask containing 30 ml of either Medium 199 containing 5% FBS [Irvine Scientific] or OptiMEM containing 1% FBS. E. tenella sporozoites, excysted by conventional techniques known to those skilled in the art, are used as inoculum 24 hours later at a rate of $1 \times 10^6$/ml. The sporozoites are left to invade for 2 hours, after which non-invaded sporozoites are removed by gentle washing. Fresh media is added to each flask. At 24 hour intervals post infection, the culture media is collected, centrifuged at 3000 × g for 30 min, and adjuvanted with 5% Amphigen. This formulation (designated 24 hour supernate, 48 hour supernate and 72 hour supernate, etc.) is stored at 4° C. until use.

B. An alternative formulation utilizes the remaining cells from the above-described vaccine. A volume of 30 ml fresh media, Medium 199 or OptiMEM, is added to the T-150 flask, and the cells are scraped into suspension. This suspension is collected, subjected to a freeze/thaw cycle, and adjuvanted with 5% Amphigen. This formulation is stored at 4° C. until use.

C. A still alternative formulation utilizes the entire infected culture from the above-described vaccine, unfractionated. Upon harvest, the infected cells are scraped into suspension. This suspension is collected, subjected to a freeze/thaw cycle, and adjuvanted with 5% Amphigen. This formulation is stored at 4° C.

EXAMPLE 4

Imunogenicity Data

A. Broiler Immunogenicity Study #1

A study was conducted to screen *E. tenella* cell culture-derived antigens for immunogenicity in commercial broilers comparing Amphigen and Freund's Complete Adjuvant (FCA) as adjuvants for the primary immunization.

Three hundred 4 day old straight run commercial broiler chicks were divided among twenty groups (15 birds per group and wing-banded) as follows. PSP refers to parasite-specific protein which is quantitated using the direct SPZELISA described in Example 2 above.

| GROUP | TREATMENT-AMPHIGEN | PSP | GROUP | TREATMENT-FCA | PSP |
|---|---|---|---|---|---|
| 1A | Unchallenged control | 0 µg/ml | 1B | Unchallenged control | 0 µg g/ml |
| 2A | Challenged control | 0 | 2B | Challenged control | 0 |
| 3A | 24 h antigen | 0.70 | 3B | 24 h antigen | 0.35 |
| 4A | 48 h antigen | 1.40 | 4B | 48 h antigen | 0.70 |
| 5A | 72 h antigen | 1.40 | 5B | 72 h antigen | 0.70 |
| 6A | 24/48 h (1:1) | 1.10 | 6B | 24/48 h (1:1) | 0.60 |
| 7A | 24/48/72 h (1:1:1) | 1.20 | 7B | 24/48/72 h(1:1) | 0.60 |
| 8A | 24 h primary/ 48 h boost | 0.7/1.4 | 8B | 24 h primary/ 48 h boost | 0.35/0.7 |
| 9A | 5 × 500 Trickle | | 9B | 5 × 500 Trickle | |

Chicks in Groups 1–8 were immunized subcutaneously (sc) at 4 days of age as designated, and boosted orally with the same amount of antigen in 5% Amphigen at 7 days of age. Both control groups received 1 ml inoculations of tissue culture medium (Gibco Medium 199+1% FBS) adjuvanted to 5% Amphigen or 1:1 with FCA [SIGMA]. Antigen for Groups 3–8 was prepared from host cell clones F7(P24–31) for the 24 hour antigen and F7(P24–29) for both 48 hours and 72 hours antigens. Antigens were stored at –20° C. until use or subjected to one freeze-thaw cycle.

*E. tenella* oocysts for groups 9A and 9B were administered orally, 500 oocysts per day for 5 consecutive days (Lilly Strain #65 strain, Lilly, Colo.) [gift from University of New Hampshire (UNH)]. In addition, group 9B birds received a s.c. injection of 50% FCA at 4 days of age.

Groups 2–9 were challenged with 35,000 L.S. #65 *E. tenella* oocysts (number determined by titration) at 21 days of age. At this time, body weights of all chicks were measured, and feed consumption monitored during the pre-patent period. Six days post challenge, body weights, feed consumption and cecal lesion scores were measured.

The clinical data from Trial #1 has been summarized in Tables 1 and 2. All least squares statistical comparisons for weight gain were made between vaccinates the unimmunized/challenge (UI/C) control group. Main effects tested included Treatment, Pens within Treatments, Sex, and a Sex by Treatment Interaction. Both Amphigen and FCA data sets were tested separately. For both data sets a significant interaction with treatment permitted analysis across sexes. No sex effect was measured for lesion score. Feed conversion was tested for only treatment effects.

In the following table, UI/UC means UnImmunized/UnChallenged; and Ag represents antigen.

TABLE 1

Clinical results of Trial #1 - Amphigen

| TREATMENT | N | WEIGHT GAIN | FEED CONVERSION | LESION SCORE |
|---|---|---|---|---|
| UI/UC | 13 | 287 | 1.8 | 0 |
| UI/C | 13 | 223 | 2.1 | 2.5 |
| 24 hour Ag | 14 | 255 | 1.9 | 2.9 |
| 48 hour Ag | 14 | 223 | 2.1 | 2.9 |
| 72 hour Ag | 15 | 264# | 1.5* | 2.8 |
| 24/48 hour Ag | 14 | 261# | 2.0 | 2.8 |
| 24/48/72 hour | 14 | 262# | 2.0 | 2.6 |
| 24->48 hour | 15 | 273* | 1.9 | 2.6 |
| Trickle | 6 | 257 | 1.8 | 2.8 |

*p < 0.05
p < 0.1

TABLE 2

Clinical results of Trial #1 FCA

| TREATMENT | N | WEIGHT GAIN | FEED CONVERSION | LESION SCORE |
|---|---|---|---|---|
| UI/UC | 15 | 286 | 1.8 | 0 |
| UI/C | 15 | 243 | 2.0 | 2.7 |
| 24 hour Ag | 15 | 260 | 1.9 | 3.0 |
| 48 hour Ag | 14 | 233 | 2.1 | 2.6 |
| 72 hour Ag | 15 | 231 | 2.6 | 2.8 |
| 24/48 hour Ag | 14 | 253 | 1.9 | 2.9 |
| 24/48/72 hour | 15 | 196* | 2.3 | 2.9 |
| 24->48 hour | 15 | 215 | 2.2 | 2.5 |
| Trickle | 15 | 266 | 1.9 | 1.5* |

*p < 0.05

Amphigen adjuvanted cell culture antigens administered sc at 4 days of age and orally at 7 days of age elicited significant (p<0.05) or near significant (p<0.1) weight gain protection to a 35,000 *E. tenella* oocyst challenge in battery cages. The regimen of 24 hours antigen s.c. followed by 48 hours antigen orally elicited significant weight gain performance, while gains sustained by the 72 hours antigen and combinations 24/48 hours and 24/48/72 hours approached significance. None of the Amphigen adjuvanted treatments affected a reduction in lesion scores. Only the 72 hours antigen vaccinated group showed a significant enhancement of the feed conversion ratio. The trickle oocyst immunized groups did not test significant for protection.

Cell culture adjuvanted with FCA elicited no significant protection to challenge, measured by weight gain or feed conversion. In fact the group immunized with the 24/48/72 hours antigen combination had significantly lower weight gains than the challenge control group. Only the trickle oocyst group had a significant reduction in lesion scores.

The following conclusions can be drawn from this data. The regimen of 24 hours s.c./48 hours oral vaccine elicited significant weight gain protection to challenge when adjuvanted with Amphigen. The 72 hours antigen and combinations of 24/48 hours and 24/48/72 hours antigens, all adjuvanted with Amphigen, also showed indications of protection in terms of weight gain. These findings suggest that each antigen preparation contains either a different composite of antigens or a different ratio of similar antigens.

Weight gain protection was measured in the absence of any reduction in lesion scores, indicating that these parameters are affected by different mechanisms. Weight gain and feed conversion performance may be sustained even in the presence of cecal lesions.

While the 48 hours antigen alone was ineffective, this antigen in combination with the 24 hours and/or 72 hours antigens or administered orally at 7 days may be critical to establishing immunity to challenge. It is assumed that the 72 hours antigen harvest contains a composite of antigens representative of all three time points.

FCA was not successful in potentiating immunogenicity of cell culture antigens. FCA alone may be eliciting a non-specific response to challenge as indicated by the higher challenge control weight gains in the FCA data set.

The importance of the oral dose, its time of administration, and subsequent impact on performance in a floor pen design including a grow-out following challenge is evaluated in the following studies (part B).

B. Broiler Immunogenicity Study #2

The purpose of this study was to screen several *E. tenella* cell culture-derived antigens for immunogenicity in commercial broilers using floor pens, and including a 40 day grow-out.

Two hundred fifty 4 day old male commercial broiler chicks were divided among ten groups (25 birds per group and wing-banded) as follows. In the table, UI/UC/Med means UnImmunized/UnChallenged/Medicated; UI/UC/Unmed means UnImmunized/UnChallenged/UnMedicated; and UI/C/Unmed means UnImmunized/Challenged/UnMedicated.

| GROUP | TREATMENT | PSP per dose |
|---|---|---|
| 1 | UI/UC/Med | 0 μg/ml |
| 2 | UI/UC/UnMed | 0 |
| 3 | UI/C/UnMed | 0 |
| 4 | 24 hours, 4 d | 2 μg/ml |
| 5 | 24 hours, 4 d/7 d | 2 μg/ml |
| 6 | 72 hours, 4 d | 2 μg/ml |
| 7 | 72 hours, 4 d/7 d | 2 μg/ml |
| 8 | 24/48 hours, 4 d | 2 μg/ml |
| 9 | 24/48 hours, 4 d/7 d | 2 μg/ml |
| 10 | 24 hours, 4 d | 2 μg/ml |
|   | 48 hours, 7 d | 1.6 μg/ml |

All chicks were held on wire until 4 days of age. At that time, chicks in Groups 1–10 were immunized s.c. and placed into clean litter floor pens as designated. Chicks in Groups 5, 7, 9 and 10 were boosted orally as designated at 7 days of age. Control groups received 1 ml inoculations of tissue culture medium (Gibco Medium 199+1% FBS) adjuvanted to 5% Amphigen. In addition, Group 1 was given feed medicated with stenerol, at 3 ppm, throughout the study. Antigen for Groups 4–10 was prepared from host cell clones F7(P24–24) and adjuvanted with 5% Amphigen.

All chicks were fed a starter ration through 27 days of age, and switched to a grower ration for the day 27–40 grow-out. Feed and water were provided ad libitum.

All birds in groups 3–10 were challenged with 35,000 (dose determined by titration) L.S. #65 *E. tenella* oocysts at 21 days of age. At this time, body weights of all birds were measured, and feed consumption monitored during the pre-patent period.

Six days post challenge, body weights and feed consumption were measured. In addition, five birds from each pen were selected randomly for cecal lesion scoring. All remaining birds were switched to a grower ration and continued until 40 days of age. During this time both weight gain and feed consumption were monitored. At day 40, all birds were sacrificed for cecal lesion scoring.

The clinical data from Trial #2 has been summarized in Table 3. All least squares statistical comparisons for weight gain were made between the unimmunized/challenge (UI/C) control group and each individual treatment group (not with the medicated control group). No statistics were performed on lesion score or feed date (one observation/group).

TABLE 3

Clinical results of Trial #2

| TREATMENT | (21 d–27 d) GAIN | FEED | LESIONS | (27 d–40 d) GAIN | FEED |
|---|---|---|---|---|---|
| UI/UC/MED | 378 | 1.84 | 0/0 | 848 | 2.20 |
| UI/UC/UNMED | 324 | 1.97 | 0/2.4 | 764 | 2.34 |
| UI/C/UNMED | 334 | 1.91 | 2.4/0.8 | 719 | 2.48 |
| 24 h-4 d | 307 | 1.98 | 2.0/1.6 | 734 | 2.49 |
| 24 h-4 d/7 d | 336 | 1.90 | 2.8/2.0 | 791* | 2.26 |
| 24 h-48 h-4 d | 301 | 2.01 | 3.0/2.2 | 774 | 2.32 |
| 24/48 h-4 d/7 d | 283 | 2.26 | 1.0/0 | 767 | 2.37 |
| 24 h–>48 h | 250 | 2.52 | 1.2/0.4 | 787# | 2.17 |
| 72 h-4 d | 282 | 2.10 | 2.2/0.4 | 781# | 2.16 |
| 72 h-4 d/7 d | 342 | 1.82 | 2.2/1.4 | 894** | 1.98 | p < 0.05
*p < 0.01
**p < 0.001

Prior to this study, *E. tenella* had not been used experimentally in this set of ten floor pens, and no cecal lesions were detected in the UI/UC/Unmed group (there was a possibility that *E. tenella* could have been cycling prior to challenge in the other pens). However, *E. acervulina* was used previously in the same set of floor pens, and upper intestinal lesions characteristic of this species were detected in the UI/UC/Unmed group.

Although not statistically significant at 6 days post challenge, only the group receiving the 72 hours antigen 4 day s.c./7 day oral showed weight gain higher than challenge controls and feed conversions lower than the medicated control group. Following the 40 day grow-out, this same 72 hours antigen vaccinated group showed highly significant ($p \leq 0.001$) protection over challenge controls in terms of weight gain, and a lower feed conversion ratio. In addition, the 24 hours antigen administered s.c. at 4 days followed by the 48 hours antigen orally at 7 days all elicited significant protection in terms of weight gain over challenge controls and comparable or better feed conversions than the medicated controls following the 40 day grow-out. The 24 hours 4 day/48 hours 7 day antigen regimen (group 10) as well as the 24/48 hours 4 day s.c./7 day oral treatment elicited lower intestinal lesion scores 6 days post challenge. No intestinal lesions were detected following the grow-out, although a general thickening of the mucosa was observed in the challenge control group. It is reasonable to assume that protection against *E. tenella,* measured during the grow-out, was elicited in the presence of cycling *E. acervulina.*

The following conclusions can be drawn from the data. Performance protection (weight gains) may be difficult to measure in floor pens 6 days following oocyst challenge at 21 days of age. A grow-out to at least 40 days may be required to demonstrate significant vaccine efficacy in floor pens.

The 72 hour antigen given once s.c. at 4 day or twice 4 day s.c./7 day oral elicited significant protection over challenge controls. The 72 hours antigen given twice sustained performance comparable to that measured in the medicated control group. This protection was demonstrated in the presence of a 35,000 *E. tenella* challenge and *E. acervulina* cycling in the litter. This is the first demonstration of an inactivated coccidiosis vaccine efficacy in a floor pen system.

The 24/48 hours antigen administered 4 day s.c./7 day oral and the regimen of 24 hours antigen given 4 day s.c. and the 48 hours antigen given 7 day oral elicited the greatest reduction in intestinal lesion scores for both *E. acervulina* and *E. tenella*. This two dose regimen 4 day S.C. followed by 7 day oral appears to be better than a single s.c. immunization at 4 day.

EXAMPLE 5

In Vitro Drug Screening

Microcultures of infected cells (in presence of $^3$H-uracil) were established at time T=0, using $\log_2$ dilutions of alpha-amanitin beginning with 50 µg/ml. Cultures were then harvested at 1 hour, 6 hours, 12 hours, 24 hours and 48 hours post infection, and label incorporation of radioactive precursor was determined by harvesting and processing for scintillation counting. When alpha-amanitin was present during the first 24 hours of parasitism, incorporation of counts (parasite material) was halted. However, if the alpha-amanitin was added after 24 hours, no inhibition of label incorporation was observed.

EXAMPLE 6

Immune Measurements

One-day old inbred chickens ($B^{19}B^{19}$ and $B^{30}B^{30}$ MHC haplotype) [New Hampshire Poultry Research Center], originally derived from the UCD.003 line, were used. Chicks were fed a nonmedicated starter/grower diet and water ad libitum. Birds were used between 1 and 43 days of age.

To simulate natural immunity, one-day old chicks were immunized with live *E. tenella* (Lilly Strain #65) oocysts for five consecutive days (500 oocysts/day) or artificially immunized at various doses with vaccine antigens (adjuvanted to 5% Amphigen). Typically, 1- or 4-day old birds were immunized subcutaneously (s.c.) in a 1.0 ml volume at the base of the neck and then boosted with vaccine adjuvanted antigens at 4 or 7 days of age by oral gavage in a 1.0 ml volume. Sham immunized (media plus 5% Amphigen) chickens were used as controls. In some experiments, chickens were challenged at 10 days of age by oral inoculation with 35,000 *E. tenella* oocysts.

A. Vaccine and Parasite antigens

Media from *E. tenella* infected F7 cells, collected at 24, 48 and 72 hours post-infection was used as the source of antigen for immunizations and for in vitro assays. For immunizations, media collected from infected F7 cells contained 1% FBS and for in vitro assays infected media collected was serum-free (0.1% FBS). Antigen-containing media was clarified by centrifugation (800× g, 30 minutes, 4° C.), aliquoted and stored at −20° C. until use. All cell-free supernatants (SN's) were quantitated for parasite-specific protein (PSP) using the direct SPZELISA. Fractionated samples were pooled according to PSP and Western reactivity. Sporozoite (SPZ) and merozoite (mrz) antigen were prepared by sonication on ice in serum-free 199 media followed by centrifugation (800× g, 10 min, 4° C.). Protein concentrations were determined by the method of Bradford, *Anal. Biochem.*, 72:248–252 (1976). Sonicated parasite suspensions were adjusted to a final concentration of 10 µg/mL in serum-free Medium 199, aliquoted, and stored at −20° C. until use.

B. Cell Isolation

Peripheral blood lymphocytes (PBL) and spleen cells were obtained from naturally or artificially (vaccine)-immunized or immunized/challenged birds at various time points post-immunization. PBL obtained by cardiac puncture were isolated by Histopaque 1077 (400× g, 15 minutes, room temperature) centrifugation of heparinized blood samples. In some assays, red blood cells from gradients were also saved and used as co-stimulants for in vitro proliferation assays. Single cell spleen suspensions were obtained by disruption of minced tissues by syringe cannulation, followed by slow speed centrifugation (50× g, 10 minutes, room temperature) and subsequent centrifugation over Histopaque 1077 gradients. Viable cell counts were performed using trypan blue and a hemacytometer.

C. Production of Antigen and Mitogen-Stimulated Cell Supernatants

Undiluted serum-free antigens, various concentrations of Conconavalin A (Con A) or alipopolysaccharide (LPS), or serum-free Medium 199 (1.0 ml/well) were cultured with lymphocytes at 40° C., 5% $CO_2$. After 24, 48 and 72 hours supernatants were removed from wells and clarified by centrifugation (800× g, 15 minutes, room temperature). α-methyl mannoside (α-MM) was added to Con A-containing supernatant to a final concentration of 50 mM. Supernatant samples were aliquoted into 1.5 ml tubes and stored at −80° C. until use. Media produced from 0–48 hour (24/48) or 48–72 hour (72) post-infection was collected, fractionated by S-Sepharose using a linear NaCl gradient, and pooled based on PSP and Western reactivity. Fraction I represents a pool of 8 fractions taken from the first part of the total fractions collected. Fraction II represents a pool of fractions numbers 9–14 and Fraction III a pool from 15–18.

D. Cell Proliferation Assays

Ten µg total protein from each fraction was assayed for reactivity in the cell proliferation assay described below.

Cells were adjusted to $10^7$ cells/ml in complete serum-free Leibovitz's Modified Hahn's media (cLMH) which contains equal parts McCoy's 5A and Leibovitz's media, $5 \times 10^{-5}$ 2-mercaptoethanol, 5 ug/ml insulin, 2 mM L-glutamine, 100 U/ml penicillin/streptomycin, 0.25 ug/ml amphotericin B, 2% tryptose phosphate, and 1 mM sodium pyruvate. Red blood cells ($10^7$/ml) were added (0.05 ml/well) to all wells of round-bottomed microliter plates. Undiluted serum-free antigens, Con A, or serum-free Medium 199 (0.1 ml/well) were thawed in a 37° C. water bath and added in quadruplicate, followed by PBL or spleen cells (0.05 ml/well). For mitogen and antigen proliferation assays, cultures were incubated at 40° C., 5% $CO_2$ for 72 or 96 hours respectively, and then pulsed with 1 µCi/well$^3$[H]-thymidine (specific activity, 5.0 µCi/mmol) during the final 18 hours of culture. Cells were harvested onto glass fiber mats using a MACHIII harvester and radioactivity determined in a Packard Matrix 96 Direct Beta Counter. High and low cpm for each sample were discarded. Except where specified, results were expressed by a stimulation index (S.I.) according to the formula:

$$S.I. = \frac{\left(\frac{\text{mean } cpm \text{ "immune" cells + antigen}}{\text{mean } cpm \text{ "immune" cells + media}}\right)}{\left(\frac{\text{mean } cpm \text{ "naive" cells + antigen}}{\text{mean } cpm \text{ "naive" cells + media}}\right)}.$$

Splenic lymphocytes from naturally immune birds were found to proliferate in response to *E. tenella*-infected-biochemically separated fraction II from a S-Sepharose column. Splenic lymphocytes obtained from 25-day old naturally immune birds showed higher S.I. values to fraction II compared to fractions I and III (Table 4).

TABLE 4

| Fraction | | S.I. Value |
|---|---|---|
| 24/48 | I | 1.1 |
| 72 | I | 0.6 |
| 24/48 | II | 2.8 |
| 72 | II | 2.5 |
| 24/48 | III | 2.0 |
| 72 | III | 0.6 |

E. T-cell Westerns

Pooled fraction 72-II was separated by one-dimensional SDS-PAGE and transferred to nitrocellulose, solubilized and assayed for reactivity in the T-cell Western proliferation assay as described below.

One-dimensional immunoblotting studies were conducted by using a modification of the method of Lamb and Young, Immunol., 60:1 (1987). Briefly, pooled fractions from S-Sepharose were separated by sodium dodecyl sulfate (SDS)-polyacrylamide gel electrophoresis (PAGE) under reducing conditions on 10 or 12.5% acrylamide mini-gels. The separated proteins were transferred to nitrocellulose (pore size, 0.2 $\mu$M) and the nitrocellulose cut into 12 equal sections corresponding to different molecular weight ranges. Nitrocellulose pieces were solubilized according to the method of Abou-Zeid, J. Imm. Methods., 98:5 (1987) using DMSO/carbonate-bicarbonate precipitation followed by freeze-thawing in deionized $H_2O$. Solubilized, microparticulate samples were washed 3x in serum-free cLMH and resuspended in a final volume of 1.0 ml serum-free cLMH. Samples were stored at −20° C. until use. For assays, samples were thawed at room temperature, diluted 1:5 in serum-free cLMH, and added in quadruplicate (0.1 ml/well) to round-bottomed microliter plates containing $5\times10^5$ red blood cells (0.05 ml/well). PBL or spleen cells ($10^7$ cells/ml, 0.1 ml/well) were then added to plates and cultures incubated at 40° C., 5% $CO_2$. Cultures were pulsed with 1 $\mu$Ci/well$^3$[H]-thymidine during the final 18 hours of culture, harvested and counted as previously described. Results are expressed as S.I. in Table 5 according to the above formula.

PBL from naturally immune birds also proliferated in response to a restricted number of E. tenella 72-II fractions. PBL obtained from 16-day old naturally-immunized/challenged birds showed the highest S.I. reactivity to three discrete areas of the immunoblot corresponding to antigens of approximate relative molecular weights ($M_TS$) of 68–75, 38–41, and 27–30 kDa (Table 5). Similar parasite proteins of approximate $M_TS$ of 25–28 and 38–40 kDa were also identified in crude, concentrated 72 hour antigen by Western using sera from these same naturally-immunized/challenged birds.

TABLE 5

| 72-II Fraction # | $M_TS$ Range(kDa) | S.I. Value |
|---|---|---|
| 2 | 97–150 | 1.2 |
| 3 | 75–97 | 1.2 |
| 4 | 68–75 | 2.3 |
| 5 | 55–68 | 1.1 |
| 6 | 48–55 | 1.5 |
| 7 | 41–48 | 1.3 |
| 8 | 38–41 | 1.9 |

TABLE 5-continued

| 72-II Fraction # | $M_TS$ Range(kDa) | S.I. Value |
|---|---|---|
| 9 | 35–38 | 1.3 |
| 10 | 30–35 | 1.3 |
| 11 | 27–30 | 2.5 |
| 12 | 22–26 | 1.2 |

F. TNF Assay

Mouse L929 cells [ATCC] were suspended in McCoys 5A/5% fetal calf serum (FCS) to $4\times10^5$ cells/ml and 0.1 ml added to flat-bottomed microliter plates. After overnight incubation at 37° C., 5% $CO_2$, $\log_2$ dilutions of mouse recombinant tumor necrosis factor (TNF) standard [Genzyme] (2 $\mu$g/ml initial concentration) or test supernatants were prepared in media in the absence or presence of actinomycin D (2 $\mu$g/ml) and added in duplicate to the appropriate wells. Following incubation for 48 hours at 37° C., 5% $CO_2$, plates were washed 1x in Dulbecco's Phosphate-Buffered Saline (DPBS) and cells fixed for 10 minutes at room temperature in methanol/acetic acid (3:1). Plates were stained for 10 minutes with 0.5% crystal violet/20% methanol and rinsed several times in $dH_2O$. After washing, 0.1 ml/well acetic acid (33%) was added and plates allowed to mix on an orbital shaker until stain was uniformly distributed throughout wells. Absorbance of wells at 600 nm was determined in a Molecular Devices $V_{max}$ automated microplate reader. Data is recorded as % cytotoxicity according the formula:

$$\% \text{ cytotoxicity}_{dil} = A_{cont} - A_{dil}/A_{cont}$$

where % cytotoxicity$_{dil}$ represents the amount of cell destruction at a given dilution, $A_{cont}$ represents absorbance in control wells (media alone) and $A_{dil}$ represents absorbance at a given dilution of test supernatant. Titer was defined as the reciprocal of the dilution necessary to achieve 50% cell cytotoxicity.

TABLE 6

Summary of Results from TNF Assay

| Treatment | Age of Bird | Stimulant | Cytotoxic Activity** |
|---|---|---|---|
| 5 × 500* | 10 | mrz | + |
| 5 × 500 | 25 | mrz | + |
| | | 72 h | − |
| | | conconavalin A | − |
| UI | 25 | mrz | + |
| | | 72 h | − |
| | | conconavalin A | − |

*5 × 500 designates doses of 500 oocysts per day for 5 days.
**(+) designates cytotoxic activity was present but reciprocal titer could not be determined.

G. Interleukin 2 Assay

IL2 responder cells were isolated from the spleens of naive 2–4 week old $B^{30}$ $B^{30}$ birds. Single cell suspensions were adjusted to $5\times10^6$ cells/ml in serum-free cLMH containing 2.5 $\mu$g/ml Con A and incubated at 40.5° C., 5% $CO_2$ in T-75 flasks. After 48 hours, nonadherent cells were treated with 50 mM $\alpha$-MM for 20 minutes at 40.5° C. and blast cells isolated by centrifugation over Histopaque 1077. Viable cells were resuspended in serum-free cLMH/100 mM $\alpha$-MM to $2\times10^6$/ml and added to round-bottomed microliter plates (0.1 ml/well.) Log$_2$ dilutions of laboratory standard IL2-containing conditioned media were added in quadruplicate to appropriate wells, and serves as a positive control. Serum-free cLMH (negative control) or test supernatant were then added (0.1 ml, 25% v/v final well concentration) in quadruplicate and plates incubated at 40° C., 5% CO$_2$ for 48 hours. Cultures were then pulsed with 1 μCi/well (0.05 ml) $^3$[H]-thymidine for an additional 6 hours. Cells were harvested and counted as previously described. High and low cpm for each sample were discarded. Supernatants considered positive for IL2 are those with mean cpm values at least two-fold that of serum-free control media from each plate.

H. Secondary In Vitro Antibody Assay (SIBA)

Log$_2$ dilutions of antigen (SPZ, mrz, or cell culture antigens) were prepared in 10 mM borate buffer, pH 9.0, at an initial concentration of 1 μg PSP/ml and 0.1 ml/well added to Nunc Immuno-Maixsorb ELISA plates. After overnight incubation at 4° C., wells were blocked using PBS/0.05% Tween 20 (PBS-T) containing 5% skim milk (0.2 ml/well) for 2 hours at 37° C. Plates were washed 3× in complete HBSS, 25 mM Hepes, pH 7.4, 1× antibiotic/antimycotic (CHBSS) and sterilized by UV-irradiation for at least 20 minutes under a sterile hood. PBL or spleen cells were adjusted to 2×10$^7$ cells/ml and 0.2 ml added to the first column. Log$_2$ dilutions of cells were then made across the entire plate in serum-free cLMH (excluding the last column for each plated antigen) to complete the checkerboard titration. Wells were brought up to a final volume of 0.2 ml using a cLMH and plates incubated for 3 to 5 days at 40.5° C., 5% CO$_2$. After incubation, plates were vigorously washed 3× using cold PBS-T.

The last column for each plated antigen was incubated with 0.1 ml of *E. tenella* hyperimmune chicken sera (1:2000 in PBS-T/0.05% BSA) for 1 hour at 37° C. After 3× washes in PBS-T, biotinylated goat anti-chicken IgG (1:2000 in PBS-T/2% skim milk) was added to all wells and incubation continued for 1 hour at 37° C. Following 3× washes in PBS-T, wells were treated with horseradish-peroxidase labelled streptavidin (1:1000 in PBS-T/2% skim milk) for an additional 1 hour. Plates were thoroughly washed in PBS-T and bound enzyme detected using TMB/peroxidase substrate. The enzymatic reaction was stopped after 15 minutes by the addition of 1M HCl, and the optical density measured at 450 nm in a Molecular Devices V$_{max}$ automated microplate reader.

TABLE 7

Secondary In-Vitro B Cell Assay

| Treatment Group | Antigen | OD at 450 nm |
|---|---|---|
| 5 × 500 | 72 h | 1.567 |
| | UI | 0.910 |
| | mrz | 1.750 |
| UI | 72 h | 0.920 |
| | UI | 0.592 |
| | mrz | 0.689 |

I. Parasite Inhibition Assay (PIA)

The QT-35 cell line (QT35 was provided as a gift from the Department of Veterinary Services, College of Agriculture, Pennsylvania State University), grown in Opti-MEM/1% FBS, was seeded at 1×10$^4$ cells/well in 96-well flat bottom plates. Following an overnight incubation at 40° C., 5% CO$_2$, cells were pretreated with duplicate log$_2$ dilutions of positive control conditioned media or test supernatant. One row was pretreated with media alone. Following pretreatment for 24 hours, fresh dilutions of test supernatant were added to cells along with 1×10$^5$ *E. tenella* sporozoites and 1 μCiwell$^3$[H]-uracil. Cultures were incubated for an additional 24 hours, harvested, and counted as described above. A test supernatant was considered positive when a 1:8 dilution caused a 30% reduction in mean cpm compared to untreated controls (media alone).

TABLE 8

Parasite Inhibition Assay

| Treatment | Cell Source | Age of Bird | Antigen Stimulation | % Inhibition |
|---|---|---|---|---|
| NE | LPL | 15 days | 72 h | 17% |
| | | | No antigen | 47 |
| NE/C | LPL | 15 days | 72 h | 40% |
| | | | No antigen | 54% |
| UI/C | LPL | 15 days | 72 h | 7% |
| | | | No antigen | 43% |
| Assay controls: | | | | |
| UI | Spleen | 21 days | conA | 54% |
| — | — | — | media alone | 0% |

LPL = Lamina Propria Lymphocytes
NE = Naturally Exposed (500 ooysts given daily for 5 days)

Numerous modifications and variations of the present invention are included in the above-identified specification and are expected to be obvious to one of skill in the art. For example, use of other appropriate avian pathogens is expected to produce antigens similar to the coccidia antigens described herein. Thus vaccines to pathogens other than coccidia may be designed using the teachings of the above invention. Such modifications and alterations to the compositions and processes of the present invention are believed to be encompassed in the scope of the claims appended hereto.

What is claimed is:

1. A vaccine against coccidiosis, comprising a cell culture component collected from a culture of cells of cell line SB-CEV-1\P (ATCC CRL 10497) or a cell line derived therefrom which is able to replicate the prepatent life cycle of an Eimeria avian parasite, which cells are infected with a selected Eimeria avian parasite, wherein the cell culture component is selected from the group consisting of a whole cell culture preparation, conditioned media which provides significant weight gain protection or significant improved feed conversion, intact infected host cells, disrupted infected host cells, or a combination thereof, and further comprising an oil in water adjuvant.

2. The vaccine of claim 1, wherein the cell line is SB-CEV-1\P (ATCC CRL 10497).

3. The vaccine of claim 1, wherein the cell line derived from SB-CEV-1\P is is SB-CEV-1\F7 (ATCC CRL 10495).

4. The vaccine of claim 1, wherein the cell line derived from SB-CEV-1\P is is SB-CEV-1\G7 (ATCC CRL 10496).

5. The vaccine of claim 1, wherein the parasite is *Eimeria tenella*.

6. A method for vaccinating poultry against infection by parasites causing coccidiosis, comprising administering to poultry an effective dose of a vaccine comprising a cell culture component collected from a culture of cells of cell line SB-CEV-1\P (ATCC CRL 10497) or a cell line derived therefrom which is able of replicate the prepatent life cycle of an Eimeria avian parasite, which cells are infected with a selected Eimeria avian parasite, wherein the cell culture component is selected from the group consisting of a whole cell culture preparation, conditioned media which provides significant weight gain protection or significant improved feed conversion, intact infected host cells, disrupted infected host cells, or a combination thereof, and further comprising an oil in water adjuvant.

7. The method of claim 6, wherein the cell line is SB-CEV-1\P (ATCC CRL 10497).

8. The method of claim 6, wherein the cell line is SB-CEV-1\F7 (ATCC CRL 10495).

9. The method of claim 6, wherein the cell line is SB-CEV-1\G7 (ATCC CRL 10496).

10. The method of claim 6, wherein the parasite is *Eimeria tenella.*

* * * * *